(12) United States Patent
Bender et al.

(10) Patent No.: US 10,500,012 B2
(45) Date of Patent: Dec. 10, 2019

(54) ILLUMINATED MR LOCAL COIL ARRANGEMENT

(71) Applicants: Andre Bender, Bergtheim (DE); Daniel Gareis, Höchberg (DE); Manuel Noras, Würzburg (DE); Rainer Kurth, Erlangen (DE); Volker Matschl, Bamberg (DE); Heinrich von Busch, Uttenreuth (DE)

(72) Inventors: Andre Bender, Bergtheim (DE); Daniel Gareis, Höchberg (DE); Manuel Noras, Würzburg (DE); Rainer Kurth, Erlangen (DE); Volker Matschl, Bamberg (DE); Heinrich von Busch, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 58 days.

(21) Appl. No.: 15/678,332

(22) Filed: Aug. 16, 2017

(65) Prior Publication Data

US 2018/0049841 A1    Feb. 22, 2018

(30) Foreign Application Priority Data

Aug. 18, 2016    (DE) .................. 10 2016 215 456

(51) Int. Cl.
*A61B 90/30* (2016.01)
*G01R 33/341* (2006.01)
(Continued)

(52) U.S. Cl.
CPC ............ *A61B 90/30* (2016.02); *A61B 5/0555* (2013.01); *A61B 5/1115* (2013.01);
(Continued)

(58) Field of Classification Search
CPC ............ A61B 10/0041; A61B 10/0233; A61B 2562/0214; A61B 2562/0257;
(Continued)

(56) References Cited

U.S. PATENT DOCUMENTS

2005/0107685 A1*  5/2005  Seeber .................. A61B 5/055
                                                          600/422
2006/0164086 A1*  7/2006  Kohlmuller .......... A61B 5/0555
                                                          324/307
(Continued)

OTHER PUBLICATIONS

"Invivo's Luminescence Breast Coil System Features Ergonomic Design", http://www.itnonline.com/content/invivo%E2%80%99s-luminescence-breast-coil-systemfeatures-ergonomic-design; Nov. 9, 2008.
(Continued)

*Primary Examiner* — Rishi R Patel
(74) *Attorney, Agent, or Firm* — Lempia Summerfield Katz LLC

(57) ABSTRACT

The present embodiments relate to an MR local coil arrangement and an MR unit. An MR local coil arrangement is disclosed including at least one MR antenna, an illumination unit with at least one light-generating unit to illuminate an illumination region, and a switching unit with at least one sensor to control the illumination unit.

12 Claims, 3 Drawing Sheets

(51) Int. Cl.
*G01R 33/30* (2006.01)
*A61B 5/055* (2006.01)
*A61B 10/00* (2006.01)
*A61B 10/02* (2006.01)
*F21V 23/04* (2006.01)
*A61B 5/00* (2006.01)
*A61B 5/11* (2006.01)
*G01R 33/28* (2006.01)
*F21Y 115/10* (2016.01)
*G01R 33/34* (2006.01)

(52) U.S. Cl.
CPC .......... *A61B 5/1126* (2013.01); *A61B 5/4312* (2013.01); *A61B 5/6891* (2013.01); *A61B 5/7285* (2013.01); *A61B 10/0041* (2013.01); *A61B 10/0233* (2013.01); *F21V 23/0471* (2013.01); *G01R 33/28* (2013.01); *G01R 33/30* (2013.01); *G01R 33/341* (2013.01); *A61B 2090/309* (2016.02); *A61B 2562/0214* (2013.01); *A61B 2562/0257* (2013.01); *F21Y 2115/10* (2016.08); *G01R 33/34046* (2013.01)

(58) Field of Classification Search
CPC ... A61B 5/0555; A61B 5/1115; A61B 5/1126; A61B 5/4312; A61B 5/6891; A61B 5/7285; A61B 90/30; A61B 5/055; A61B 90/13; F21V 23/0471; F21Y 2115/10; G01R 33/28; G01R 33/30; G01R 33/34046; G01R 33/341; G01R 33/34084; G01R 33/34; G01R 33/34007; G01R 33/285

See application file for complete search history.

(56) References Cited

U.S. PATENT DOCUMENTS

| 2014/0213886 | A1 | 7/2014 | Menon et al. |
| 2015/0196367 | A1* | 7/2015 | Muller ................. A61B 6/032 600/410 |
| 2017/0318644 | A1* | 11/2017 | Hartl ................. H05B 37/0227 |

OTHER PUBLICATIONS

German Office Action for related German Application No. 10 2016 215 456.7 dated Apr. 28, 2017.

* cited by examiner

ILLUMINATED MR LOCAL COIL ARRANGEMENT

CROSS-REFERENCE TO RELATED APPLICATIONS

The present patent document claims the benefit of DE 102016215456.7, filed on Aug. 18, 2016, which is hereby incorporated by reference in its entirety.

BACKGROUND

The present embodiments relate to an MR local coil arrangement and an MR device.

Magnetic Resonance Imaging is a known technique for generating images of the inside of a body of an examination subject, based on the physical phenomenon of magnetic resonance (MR). In order to achieve a high signal-to-noise ratio in the images, MR local coils are used in most cases. MR local coils are usually antenna systems fitted in direct vicinity of a patient.

In many applications it is desirable to illuminate at least part of an MR local coil arrangement. For example, a MR local coil arrangement may include a biopsy unit, which usually has scales for an operator to set coordinates when guiding a needle (e.g., for a breast biopsy, etc.). The operator scales often can only be read with difficulty due to the light conditions that are usually prevalent (e.g., due to shadowing from the room lighting). This problem arises in a medial biopsy because, in the medial intervention region, a patient's upper body often blocks light from the ceiling lighting.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, an effective and/or user-friendly illumination of an MR local coil arrangement is provided (e.g., illumination of an MR local coil arrangement including a biopsy unit).

Accordingly, an MR local coil arrangement is provided including at least one MR antenna, an illumination unit with at least one light-generating unit to illuminate an illumination region and a switching unit including at least one sensor to control the illumination unit. The MR local coil arrangement may include a housing incorporating the aforementioned units allowing for a compact design.

The MR local coil arrangement may include an MR breast coil (e.g., an MR coil that is designed for imaging a breast, particularly a female breast).

The at least one MR antenna may include one or a plurality of conductor loops for transmitting and/or receiving high frequency (HF) electromagnetic waves. The one or plurality of conductor loops may be suitable for receiving magnetic resonance signals with a high signal-to-noise ratio (e.g., because the conductor loops may be arranged close to the examination subject).

With the aid of the illumination unit, a desired illumination region may be illuminated (e.g., with light that is generated by the light-generating unit). Various procedures, such as the positioning of a biopsy needle for instance, may be carried out more easily and reliably as a result of the illumination.

With the aid of the switching unit, an operator (e.g., a medical professional such as a physician) may control the illumination unit in order to adjust an operating condition of the illumination unit. Through the operator's interaction with the at least one sensor, a switching signal may be generated. The switching unit may include one or a plurality of switches and/or one or a plurality of electric switching circuits (e.g., processors) for processing the switching signals.

With the aid of the control, the illumination unit may be switched between a least two operational states by the switching unit. For example, the switching unit may activate and deactivate the illumination unit (e.g., at least parts of the illumination unit may be switched on and off by the switching unit as required).

The illumination unit may be configured to illuminate the illumination region with light that varies in the at least two operational states with regard to the intensity and/or color of the light. For example, the at least two operational states may have a first light intensity and at least one additional light intensity (e.g., with the first light intensity is greater than the at least one additional light intensity). For example, the light may be dimmed with the aid of the switching unit (e.g., continuously). In this way, the light intensity may be optimally adjusted to the relevant requirements.

In an example, the at least two operational states include a first light color and at least one another light color (e.g., such that a change may be made from a green color to a red color). Consequently, signals may be transmitted to the patient and/or a desired atmosphere may be generated.

The switching unit may be operated in a contactless, contact-free manner. For example, the illumination unit may be controlled with the switching unit without any direct mechanical contact between an operator (e.g., a physician) and the switching unit being necessary for this purpose. Therefore, the operator may switch between a plurality of operational states of the illumination unit without touching the switching unit by hand.

Contactless operation allows for sterile use of the MR local coil arrangement because the risk of the transmission of bacteria to the switching unit may be reduced. In the medical environment, this is an advantage because hygiene requirements are usually particularly high.

One embodiment provides for the at least one sensor to include at least one proximity sensor and/or motion sensor. As a result of the proximity and/or motion sensor(s), the switching unit may be operated in a contactless manner. A proximity sensor may also be referred to as an approach sensor, a proximity switch, a proximity initiator and/or an approach switch. Proximity sensors may be understood as sensors that react to an approach in a contact-free manner (e.g., without direct contact).

The at least one proximity sensor and/or motion sensor may have a range of less than 30 mm (e.g., less than 20 mm or less than 10 mm). This range is big enough to allow a comfortable operation of the switching unit, but at the same time small enough to provide that the risk of accidental activation of the proximity sensor is low.

Here, the range of the proximity sensor is a space between the at least one proximity sensor and/or motion sensor and an object (e.g., an operator's hand) within which the at least one proximity sensor and/or motion sensor may be operated by the object. The at least one proximity sensor and/or motion sensor may react to the object as soon as the object comes within the range of the at least one proximity sensor and/or motion sensor.

The range of the at least one proximity sensor and/or motion sensor may be set through the layout and/or the configuration (e.g., by establishing one or a plurality of threshold values for the at least one proximity sensor and/or motion sensor).

The at least one proximity sensor and/or motion sensor may include at least one optical, acoustic and/or capacitive sensor. These physical phenomena are particularly well suited to use in a proximity sensor and/or motion sensor. Furthermore, such sensors are readily available and may be produced at a reasonable cost.

The at least one sensor may include at least one transmission unit and at least one receiving unit, the at least one transmission unit being configured to transmit waves, and the at least one receiving unit being configured to receive the waves transmitted by the at least one transmission unit. With such a configuration, the at least one proximity sensor and/or motion sensor may be provided. The signal received may be processed by one or a plurality of electric circuits (e.g., by processors) and/or used to control the illumination unit.

In one embodiment of the at least one proximity sensor and/or motion sensor provided as an optical sensor, the waves transmitted may include electromagnetic waves with a wavelength from a wavelength range between 700 nm and 1 mm (e.g., between 800 and 1500 nm or between 900 and 1100 nm). For example, the at least one transmission unit may include an infrared-light-emitting diode and/or the at least one receiving unit may include an infrared photodiode.

Light in this wavelength range may not be visible to the naked eye (e.g., such that no optical irritation of the operator occurs).

It is further conceivable that the transmitted waves will include mechanical waves that encompass a wavelength from a wavelength range of between 0.2 and 20 mm (e.g., between 0.5 and 5 mm). For example, the at least one transmission unit and/or the at least one receiving unit may include an ultrasonic transducer.

The at least one proximity sensor and/or motion sensor may be configured such that the at least one proximity sensor and/or motion sensor may detect a space (e.g., a space between the at least one proximity sensor and/or motion sensor and an object that is provided for operating the switching unit). For example, to this end, for a travel time measurement for an optical and/or acoustic signal to be provided, a time may be measured that occurs between a transmission point for a wave that is sent out by the transmission unit and a receiving point for this point by the receiver unit. With the propagation speed of the wave (e.g., the speed of light or the speed of sound), it is possible to infer the space between the proximity sensor and the object. For example, the light intensity may be monitored using the space that has been detected.

According to an embodiment, the switching unit may be operated via a gesture control. Consequently, operating states may be activated with deliberate swiping movements of the illumination unit.

One embodiment of the MR local coil arrangement provides for the at least one light-generating unit to be configured to beam light directly into the illumination region. Direct radiation may be understood to be the light generated by the light-generating unit that is radiated into the illumination region in a linear manner (e.g., without any detours). For example, after direct radiation has been generated by the light-generating unit, the light directly enters the air and is diffused into the illumination region.

In this way, the proposed embodiment differs from other embodiments in that the light, once generated, is first guided into a medium (e.g., by a fiber-optic cable, such as a glass fiber). For example, the at least one light-generating unit may be configured to radiate light into the illumination region in an unguided manner.

Without guided light, the MR local coil arrangement may be configured in a simpler manner. Because optical fibers may be limited in terms of the bend radius, it is likewise unnecessary to have the complex guiding of the optical fibers that this entails.

In addition, possible losses of light output in the optical fibers may be avoided from the onset (e.g., such that a higher degree of efficiency may be achieved). Consequently, the surface temperatures on the MR local coil arrangement may be kept at a low level.

The light-generating unit may include at least one light-emitting diode (LED). LEDs may be distinguished by a high level of efficiency, a compact design, and a high suitability for incorporation in the MR local coil arrangement.

One embodiment of the MR local coil arrangement provides for the illumination unit to include at least two partial illumination units arranged on the opposite sides of the MR local coil arrangement. As a result, a large region of the MR local coil arrangement may be illuminated.

For example, if the MR local coil arrangement is an MR breast biopsy coil, then on a first side a first biopsy region for the right breast may be illuminated by a first partial illumination unit and at the opposite second side a second biopsy region for the left breast may be illuminated by a second partial illumination unit. Consequently, a first part of the illumination region is arranged on the first side, and a second part of the illumination region is arranged on the second side.

The opposite sides may be separated by a central plane. The central plane being may be arranged centrally in the MR local coil arrangement and parallel to a longitudinal axis of the MR local coil arrangement. The central plane may be arranged to be in parallel with a sagittal plane (e.g., a median plane) of a patient who is to be examined using the MR local coil arrangement.

The MR local coil arrangement may be configured to be symmetrical to a symmetrical plane. The symmetrical plane may cover the same area as the central plane.

The switching unit for each of the at least two partial illumination units may include a respective partial switching unit. As a result, the partial illumination units may be operated individually.

For example, if the MR local coil arrangement is an MR breast biopsy coil, then the first partial illumination unit may be operated by a first switching unit and the second partial illumination unit may be operated by a second switching unit.

The partial switching unit for the partial illumination unit may be arranged on the same side of the opposite sides of the MR local coil arrangement. For example, the first partial switching unit is arranged on the same side as the first partial illumination unit and the second partial switching unit is arranged on the same side as the second partial illumination unit. This allows a simple and intuitive operation of the illumination unit.

The MR local coil arrangement may include a biopsy unit that is arranged, at least in part, inside the illumination region. The biopsy unit may include an aid for arranging a breast in place. The biopsy unit may also include a positioning unit (e.g., including a grid-shaped structure and/or a "Post and Pillar" system that includes one or a plurality of operator scales). The positioning unit may be used for taking precisely targeted tissue samples. For example, a lesion may be located through a diagnostic examination and the coordinates of the lesion may be determined. The coordinates that have been determined may be transposed on the positioning unit. By illuminating the biopsy unit (e.g., illuminating the operator scales of the positioning unit), a biopsy may be carried out in a more comfortable and safer manner because the operator scales may be read off more easily.

One embodiment provides for the MR local coil arrangement to include a housing. The housing includes at least one region recessed towards the inside. The at least one light-generating unit may be arranged in the region that is recessed towards the inside. Through having an arrangement that is recessed towards the inside, dazzling of the operator may effectively be avoided.

The region that is recessed towards the inside may have an area that is smaller than 100 cm$^2$ (e.g., smaller than 40 cm$^2$ or smaller than 15 cm$^2$). Furthermore, the region that is recessed towards the inside may have a depth of less than 5 cm (e.g., less than 2 cm or less than 1 cm).

Furthermore, an MR unit may be provided with at least one MR local coil arrangement according to one or more of the embodiments described in the aforementioned.

The MR device may include a patient couch. The patient couch may include a positioning plane. The light-generating unit may transmit beams of light in the direction of the positioning plane of the patient couch (e.g., the light is beamed down into the illumination region from above).

For example, the perpendicular of the positioning plane and the direction of the light beam enclose an angle that is smaller than 90°. Therefore, the light is beamed down from above, but the light is not necessarily beamed down vertically (e.g., the light may also be beamed down diagonally).

The direction of the downward beam may be achieved by the light-generating unit being arranged in a region that is apart from the positioning plane (e.g., in the upper region of the MR local coil arrangement). The space between the positioning plane and the light-generating unit may be more than 10 cm (e.g., more than 15 cm or more than 20 cm). This avoids dazzling an operator, because he or she may not be looking directly into the light that has been generated.

DETAILED DESCRIPTION

Figure 1:
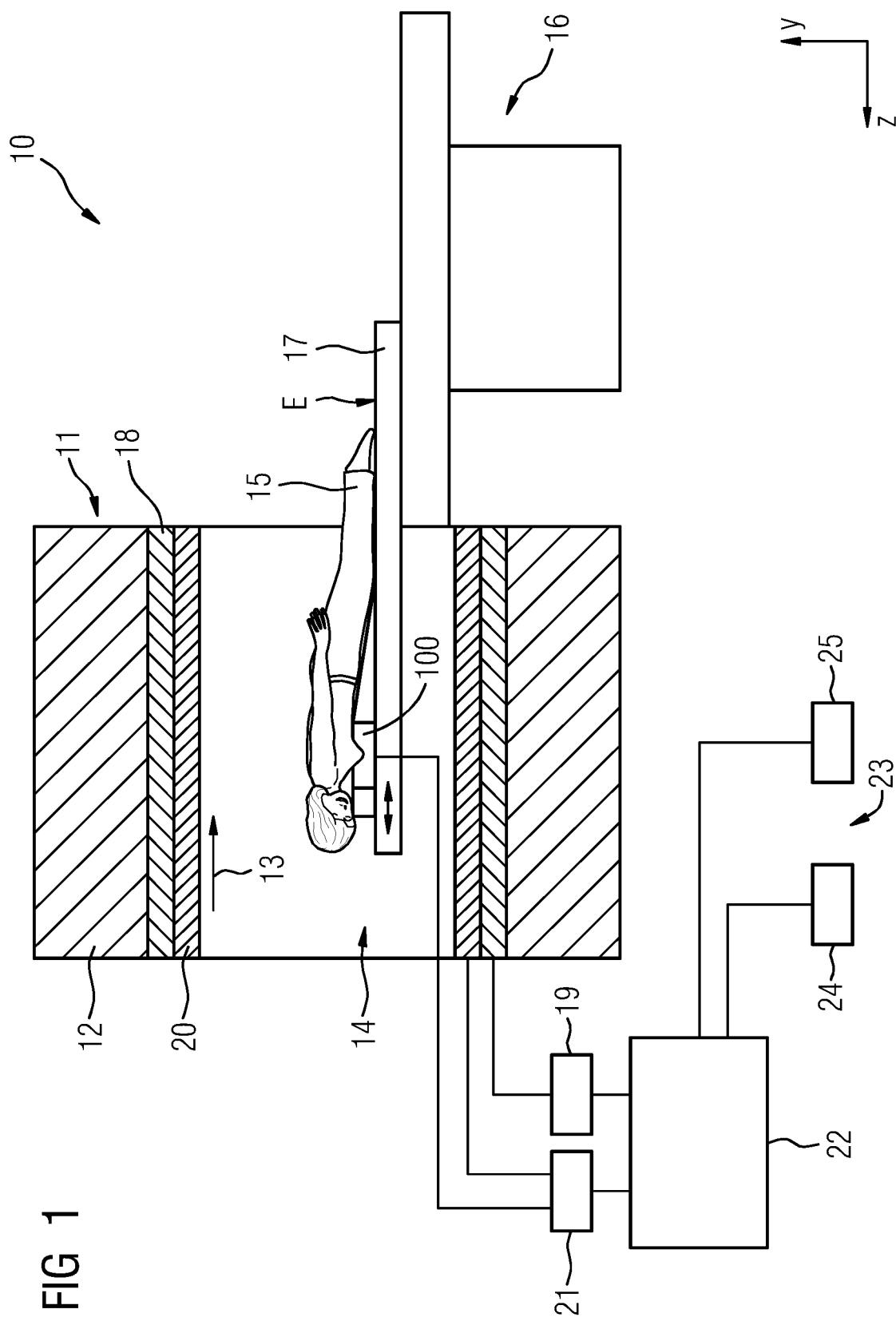
FIG. 1 shows a diagrammatic view of an MR device including an MR local coil arrangement according to an embodiment.

FIG. 1 shows a diagram of a magnetic resonance device 10. The MR device 10 includes a magnet unit 11 that includes a main magnet 12 to generate a strong main magnetic field 13 (e.g., that is constant over time). The MR device 10 includes a patient accommodation region 14 to accommodate a patient 15. In the present embodiment, the patient accommodating region 14 is cylindrical and is encompassed circumferentially by a magnet unit 11. A configuration of the patient-accommodating region 14 that deviates from the diagram of FIG. 1 may be provided. The patient 15 may be slid into the patient-accommodating region 14 using a patient-positioning apparatus 16 of the magnetic resonance unit 10. To this end, the patient-positioning apparatus 16 includes a patient table 17 that is moveably configured within the patient-accommodating region 14.

The magnet unit 11 also includes a gradient coil unit 18 to generate magnetic field gradients that are used for spatial encoding during an imaging procedure. The gradient coil unit 18 is controlled by a gradient control unit 19 of the magnetic resonance unit 10. The magnet unit 11 further includes a high frequency antenna unit 20 that, in the present embodiment, is configured as a body coil that is fixedly incorporated into the magnetic resonance unit 10. The high frequency antenna unit 20 is configured to excite atomic nuclei that appear in a main magnetic field 13 generated by the main magnet 12. The high frequency antenna unit 20 is controlled by a high frequency antenna control unit 21 in the magnetic resonance unit 10 and radiates high frequency alternating fields into an examination area that may be formed from a patient-accommodating area 14 of the magnetic resonance unit 10. The high frequency antenna unit 20 is also configured to receive magnetic resonance signals.

To control the main magnet 12, the gradient control unit 19, and the high frequency antenna control unit 21, the magnetic resonance unit 10 includes a system control unit 22. The system control unit 22 centrally controls the magnetic resonance unit 10 (e.g., by running a predetermined gradient echo imaging sequence). In addition, the system control unit 22 includes an evaluation unit (not shown in greater detail) to evaluate medical imaging data that have been mapped during a magnetic resonance examination. The magnetic resonance unit 10 also includes a user interface 23 connected to the system control unit 22. Control data (e.g., such as imaging parameters) and reconstructed magnetic resonance images may be displayed for a medical operator on a display unit 24 (e.g., on at least one monitor) of the user interface 23. The user interface 23 further includes an input unit 25 with which data and/or parameters may be input by the medical operator during a measurement procedure.

Furthermore, the patient couch 17 includes a positioning plane E, on which an MR local coil arrangement 100 is arranged. With the aid of the MR local coil arrangement 100, magnetic resonance signals may be received and forwarded to the high frequency antenna unit 21. For example, the MR local coil arrangement 100 is configured to examine the breast of the patient 15. Possible embodiments of such an MR local coil arrangement 100 are described in greater detail hereinafter using FIGS. 2 to 4.

Figure 2:
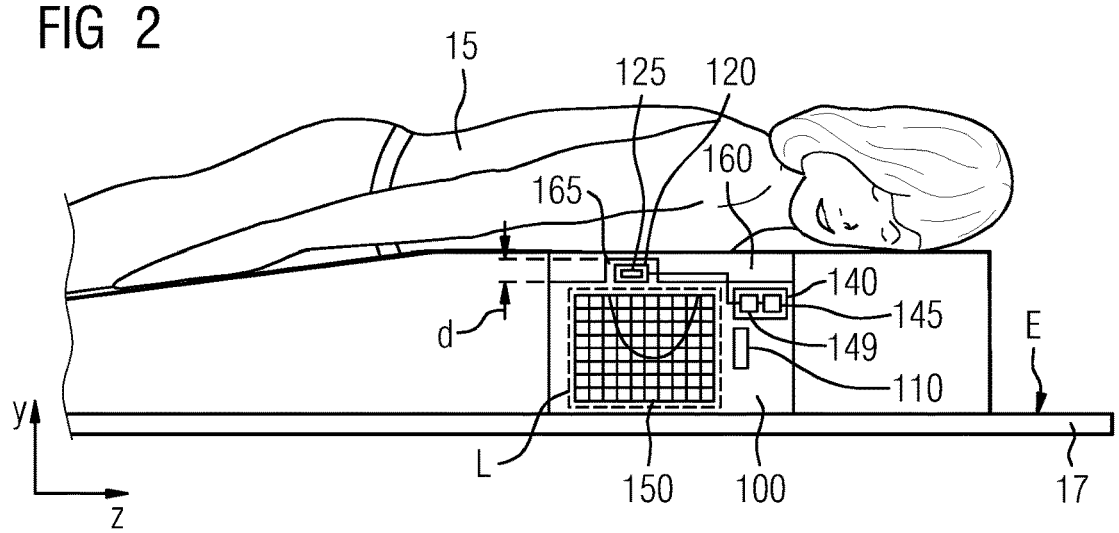
FIG. 2 shows a diagrammatic side view of an MR local coil arrangement on a patient couch according to an embodiment.

The MR local coil arrangement 100 shown in FIG. 2 includes one or a plurality of MR antennas 110 (e.g., shown here in a highly simplified form in order to provide a clear overview). An MR antenna 110 may include at least one conductor loop that is arranged close to the patient 15 in order to be able to receive the magnetic resonance signals with a high signal-to-noise ratio.

In order to illuminate an illumination region L, the MR local coil arrangement 100 includes an illumination unit 120 with at least one light-generating unit 125 (e.g., including one or a plurality of light-emitting diodes). Light-emitting diodes may have high efficiency and/or low heat loss. In order to keep the surface temperatures of the MR local coil arrangement 100 sufficiently low, the power supply to the light-emitting diodes may be set such that a sufficiently high light yield is provided and that there is still a buffer for any upper temperature limits that have to be complied with.

Within the illumination regions L, a biopsy unit 150 is provided (e.g., configured as a grid). However, other configurations may be provided, such as an arrangement of parallel rods, etc. In this example, the illumination region L completely covers the biopsy unit 150 (e.g., the light provided by the illumination unit 120 illuminates the entire biopsy unit 150). However, the biopsy unit 150 may be illuminated by the illumination unit 120 (e.g., the part that is used for positioning a biopsy needle).

Furthermore, the MR local coil arrangement 100 includes a switching unit with at least one sensor 145. The illumination unit 120 may be controlled with the aid of said switching unit 140.

The switching unit may additionally include control electronics 149 (e.g., attuned to the high-capacity alternating fields that may prevalent in MR environments). For example, to prevent flickering of the light-emitting diodes due to direct induction of alternating RF fields, the control electronics 149 may include one or a plurality of RF chokes for the corresponding frequency. Furthermore, to control the illumination unit, the control electronics 149 may include one or a plurality of switching circuits and/or microcontrollers that are configured to process signals received by the sensors 145 to control the illumination unit 120.

For example, the illumination unit 120 may be switched between at least two operational states. For example, in a first operational state, the light-generating unit 125 may be switched on (e.g., the illumination region L is illuminated) and in a second operational state the light-generating unit 125 may be switched off (e.g., the illumination region L is not illuminated).

Other operational states may be provided that differ in the intensity and/or color of the light with which the illumination region L is illuminated.

The switching unit 140 may be operated in a contact-free manner. For example, an operator (e.g., a physician) may carry out a biopsy, activate the illumination unit 125 and deactivate the illumination unit 125 without touching the MR local coil arrangement 100 when so doing.

The at least one sensor 145 includes at least one proximity sensor and/or motion sensor (e.g., an optical, acoustic, and/or capacitive sensor). For example, the range and/or sensitivity range of such sensors may be firmly set on the circuit board using the specifically installed components. A sensitive region less than 30 mm is suggested (e.g., less than 20 mm or less than 10 mm). Where there is a larger distance from the sensor, no switching procedure takes place (e.g., yet a targeted). Contactless switching is possible within the sensitivity range directly in front of the sensor (e.g., if an operator brushes closely past the sensor in order to turn the light on or off). Such sensors may also be used to operate the switching unit 140 via a gesture control.

The at least one light-generating unit 125 may be configured to radiate light directly into the illumination region L. The light is generated by the light-generating unit 125 itself and is radiated directly into the illumination region L. For example, once generated, the light does not have to be transmitted to the illumination region L in a complex manner using a fiber-optic cable or with some loss of light.

Figure 3:
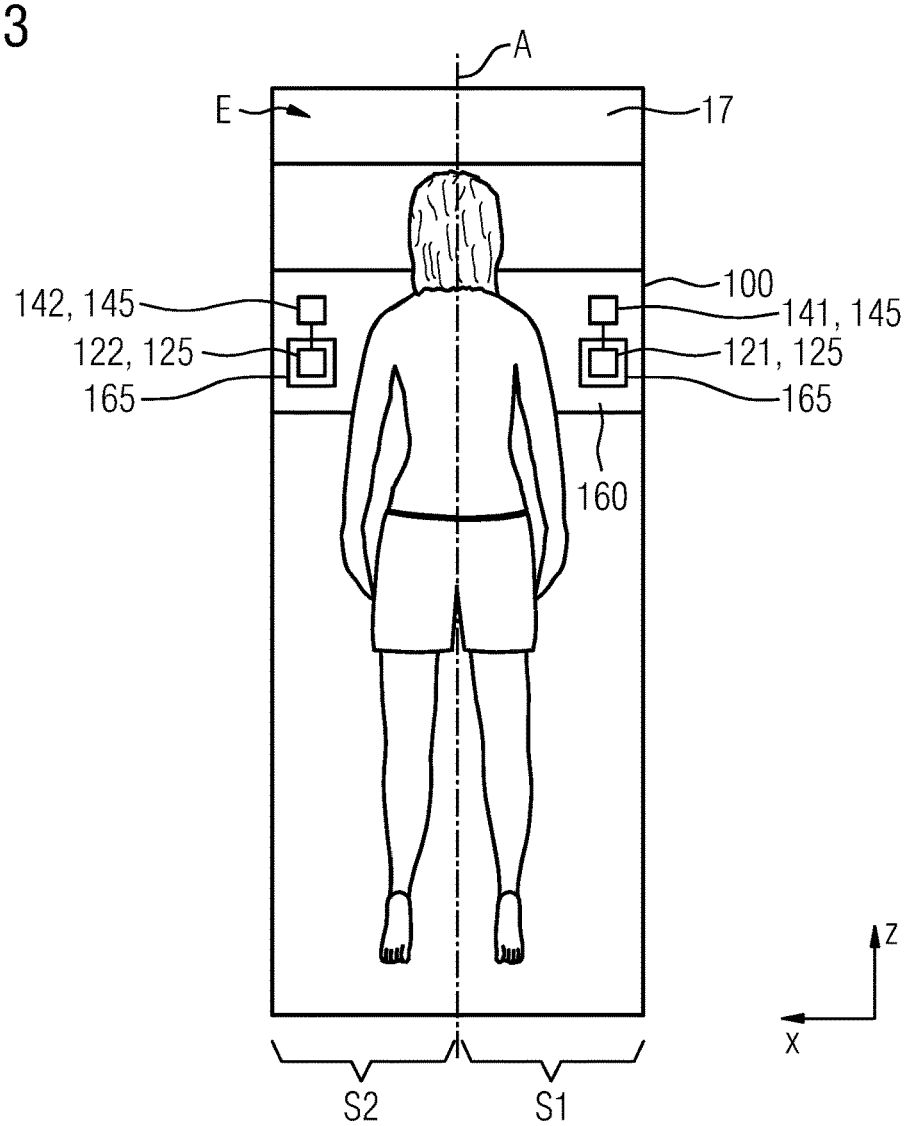
FIG. 3 shows a diagrammatic top view of an MR local coil arrangement on a patient couch according to an embodiment.

FIG. 3 shows a top view of an embodiment in which the illumination unit 120 includes two partial illumination units 121, 122 that are arranged on opposite sides S1, S2 of the MR local coil arrangement 100.

The MR local coil arrangement 100 is arranged on a positioning area E of the patient couch 17. Perpendicular to this positioning area and parallel with a longitudinal axis A (e.g., running parallel to the z-direction), a sagittal plane may be identified. If the sagittal plane is centrally located with respect to the expanse of the MR local coil arrangement in the x-direction, then this sagittal plane may also be referred to as a median plane. Through this median plane, the MR local coil arrangement 100 may be divided into the two sides S1 and S2 (e.g., depicted as the same size). In the z-axis direction of view, the two sides may be referred to as the right-hand side S1 and the left-hand side S2.

The switching unit 140 for each of the two partial illumination units 121, 122 further includes a respective partial switching unit 141, 142. For example, on the S1 side, the partial illumination unit 121 may be operated by the partial switching unit 141, and on the S2 side, the partial illumination unit 122 may be operated by the partial switching unit 142. A sensor 145 may be provided on each of the two sides S1, S2 of the MR local coil arrangement 100 (e.g., one sensor on the left and one sensor on the right). The sensors may be arranged such that for the operator (e.g., in an intervention and/or a biopsy) the sensors are easy to access but may not be activated too easily in error. Such an arrangement gives the operating personnel a high level of convenience such that the partial illumination units 121, 122 may be controlled individually. For example, the illumination may be set according to need, operating personnel and/or patient 15 (e.g., indicating both sides off, both sides on, or only one side on). Illumination that may be turned on or off selectively makes it easier to avoid any possible dazzling.

Figure 4:
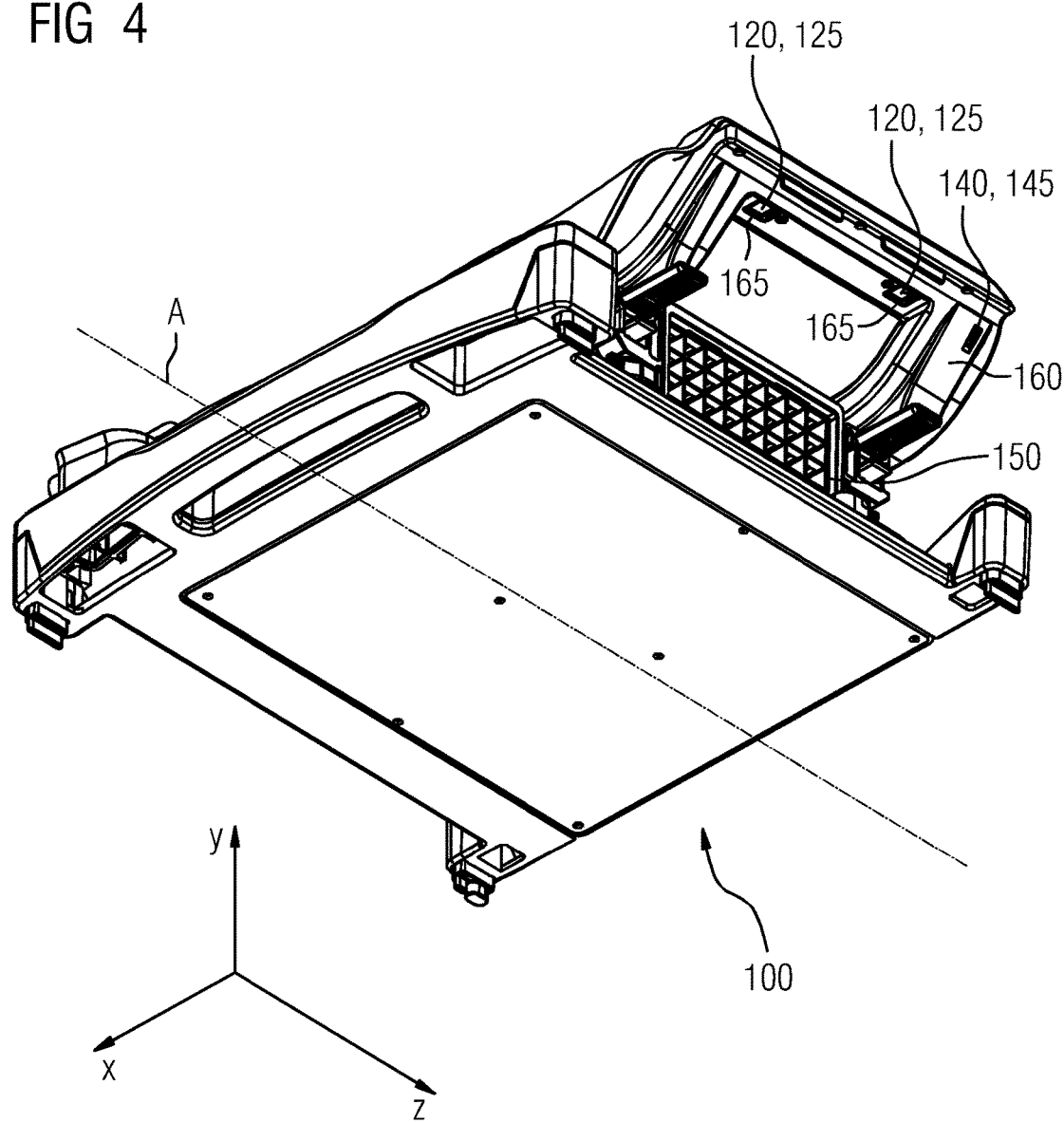
FIG. 4 shows a perspective view of an MR local coil arrangement according to an embodiment.

FIG. 4 shows a more detailed embodiment of an MR local coil arrangement 100 with one side of the MR local coil arrangement 100 being viewed in perspective laterally from below. On the side shown, there is arranged an illumination unit 120 including two light-generating units 125 and a switching unit 140 with a sensor 145. With the illumination unit 120, the biopsy unit 150 may be illuminated at least partially. In this embodiment, the biopsy unit includes a grid system. Other variants may be provided, such as a "post and pillar" system (e.g., with horizontal or vertical grids to immobilize the breast).

In the embodiments shown in FIGS. 2 to 4, the MR local coil arrangement 100 includes a housing with a plurality of regions recessed inwards 165 in which the light-generating units 125 are arranged. It is therefore possible to prevent operating personnel from being dazzled by the light-generating units 125 (e.g., the recessed regions serve as anti-glare shields).

The region recessed inwards 165 shown in FIG. 2 may have a depth of less than 5 cm (e.g., less than 2 cm or less than 1 cm). The region recessed inwards 165 shown in FIG. 3 may have an area that is smaller than 100 cm$^2$ (smaller than 40 cm$^2$ or smaller than 15 cm$^2$).

A further measure to avoid dazzling the operating personnel may be explained in FIGS. 1 to 3, showing the positioning area E of the patient couch 17 on which the MR local coil arrangement 100 is arranged in place. The light-generating unit 125 may transmit beams of light in the direction of the positioning plane E of the patient couch 17. If the propagation direction of the beams of light is described with the aid of a vector with the components x, y and z, then according to this system of coordinates, the y-component has a negative value (e.g., the light shines downwards). The operating personnel looking down from above onto the MR local coil arrangement 100 are therefore not dazzled by the light.

For example, in FIG. 4, the light-generating units 125 are each located on the underside of the outer frames of the housing, each in a corner. This makes it possible to avoid dazzling the operating personnel and at the same time provides good illumination of the biopsy unit 150.

The MR local coil arrangements and the MR device described in detail in the aforementioned are merely embodiments that can be modified in a very wide variety of ways by a person skilled in the art without departing from the scope of the invention. Furthermore, the use of the indefinite article "a" or "an" does not preclude the relevant features from being present in plurality. Likewise the term "unit" does not preclude the relevant components from consisting of a plurality of partial components that work in combination and that can optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance (MR) local coil arrangement comprising:
    at least one MR antenna;
    an illumination unit with at least one light-generating unit configured to illuminate an illumination region of a patient; and
    a switching unit with at least one sensor configured to control the illumination unit, the at least one sensor comprising at least one proximity sensor, at least one motion sensor, or the at least one proximity sensor and the at least one motion sensor,
    wherein the switching unit is configured to switch the illumination unit between at least two operational states without an operator touching the switching unit.

2. The MR local coil arrangement of claim 1, wherein the illumination unit is configured to illuminate the illumination region of the patient with light that differs in the at least two operational states with regard to an intensity of the light, a color of the light, or the intensity of the light and the color of the light.

3. The MR local coil arrangement of claim 1, wherein the at least one proximity sensor, the at least one motion sensor, or the at least one proximity sensor and the at least one motion sensor comprises at least one optical sensor, at least one acoustic sensor, at least one capacitive sensor, or a combination thereof.

4. The MR local coil arrangement of claim 1, wherein the switching unit is configured to be operated via gesture control.

5. The MR local coil arrangement of claim 1, wherein the at least one light-generating unit is configured to beam light directly into the illumination region of the patient.

6. The MR local coil arrangement of claim 1, wherein the at least one light-generating unit comprises at least one light-emitting diode.

7. The MR local coil arrangement of claim 1, wherein the illumination unit comprises at least two partial illumination units arranged on opposite sides of the MR local coil arrangement.

8. The MR local coil arrangement of claim 7, wherein the switching unit comprises a partial switching unit for each partial illumination unit of the at least two partial illumination units.

9. The MR local coil arrangement of claim 1, wherein the MR local coil arrangement comprises a biopsy unit arranged at least partly inside the illumination region of the patient.

10. The MR local coil arrangement of claim 1, further comprising:
    a housing having a region recessed inwards,
    wherein the at least one light-generating unit is arranged in the region recessed inwards.

11. A magnetic resonance (MR) device comprising:
    at least one MR local coil arrangement comprising:
        at least one MR antenna;
        an illumination unit with at least one light-generating unit configured to illuminate an illumination region of a patient; and
        a switching unit with at least one sensor configured to control the illumination unit, the at least one sensor comprising at least one proximity sensor, at least one motion sensor, or the at least one proximity sensor and the at least one motion sensor,
    wherein the switching unit is configured to switch the illumination unit between at least two operational states without an operator touching the switching unit.

12. The MR device of claim 11, further comprising:
    a patient couch having a positioning plane,
    wherein the at least one light-generating unit is configured to transmit a beam of light in a direction of the positioning plane of the patient couch.

* * * * *